United States Patent
Geddes et al.

(10) Patent No.: US 9,784,682 B2
(45) Date of Patent: *Oct. 10, 2017

(54) FLUORESCENCE MICROSCOPE IN MICROWAVE CAVITY

(71) Applicant: UNIVERSITY OF MARYLAND, BALTIMORE COUNTY, Baltimore, MD (US)

(72) Inventors: Chris D. Geddes, Bel-Air, MD (US); Michael J. R. Previte, Peabody, MA (US)

(73) Assignee: University of Maryland, Baltimore County, Baltimore, MD (US)

(*) Notice: Subject to any disclaimer, the term of this patent is extended or adjusted under 35 U.S.C. 154(b) by 1112 days.

This patent is subject to a terminal disclaimer.

(21) Appl. No.: 13/850,335

(22) Filed: Mar. 26, 2013

(65) Prior Publication Data
US 2013/0216435 A1    Aug. 22, 2013

Related U.S. Application Data

(62) Division of application No. 12/602,552, filed as application No. PCT/US2008/065801 on Jun. 4, 2008, now Pat. No. 8,404,450.
(Continued)

(51) Int. Cl.
*G01N 21/64* (2006.01)
*G02B 21/00* (2006.01)
*G02B 21/16* (2006.01)

(52) U.S. Cl.
CPC ..... *G01N 21/6486* (2013.01); *G01N 21/6458* (2013.01); *G02B 21/0004* (2013.01);
(Continued)

(58) Field of Classification Search
None
See application file for complete search history.

(56) References Cited

U.S. PATENT DOCUMENTS

| 5,017,009 A | 5/1991 | Schutt et al. |
| 5,449,918 A | 9/1995 | Krull et al. |

(Continued)

FOREIGN PATENT DOCUMENTS

| JP | 2002-277744 | 9/2002 |
| JP | 2005-195379 | 7/2005 |
| WO | WO 2004-057402 | 7/2004 |

OTHER PUBLICATIONS

Asian (2006) J Fluor 16:3-8.*
(Continued)

*Primary Examiner* — Melanie Y Brown
*Assistant Examiner* — Richard Moerschell
(74) *Attorney, Agent, or Firm* — Tristan A. Fuierer; Marianne Fuierer; Moore & Van Allen, PLLC

(57) ABSTRACT

The present invention relates to an optical imaging system communicatively connected to a microwave energy producing source wherein the combination provides for increases in chemical reaction times and the ability to monitor the reactions in real time with sufficient resolution to view the location of intracellular components labeled with luminescent molecules as well as interaction with other biomolecules and responses to localized environmental variables in living cells and tissues during the application of a microwave field.

11 Claims, 10 Drawing Sheets

Related U.S. Application Data

(60) Provisional application No. 60/932,620, filed on Jun. 4, 2007.

(52) U.S. Cl.
CPC ..... *G02B 21/16* (2013.01); *G01N 2021/6469* (2013.01); *Y10T 436/143333* (2015.01); *Y10T 436/201666* (2015.01)

(56) References Cited

U.S. PATENT DOCUMENTS

| | | | |
|---|---|---|---|
| 5,866,433 A | 2/1999 | Schalkhammer et al. | |
| 6,289,144 B1 | 9/2001 | Neuschafer | |
| 7,253,452 B2 | 8/2007 | Steckel et al. | |
| 7,348,182 B2 | 3/2008 | Martin et al. | |
| 7,351,590 B2 | 4/2008 | Martin | |
| 7,648,834 B2 | 1/2010 | Moore | |
| 7,718,445 B2 | 5/2010 | Martin | |
| 8,008,067 B2* | 8/2011 | Geddes | G01N 21/76 359/585 |
| 8,034,633 B2* | 10/2011 | Geddes | B82Y 30/00 422/21 |
| 9,075,018 B2* | 7/2015 | Geddes | G01N 21/76 |
| 2003/0082633 A1 | 5/2003 | Martin et al. | |
| 2005/0133724 A1* | 6/2005 | Hsieh | B01L 7/52 250/339.12 |
| 2006/0120603 A1* | 6/2006 | Li | G06K 9/00127 382/181 |
| 2008/0231939 A1 | 9/2008 | Gluckstad | |
| 2009/0200232 A1* | 8/2009 | Mattiasson | B01D 15/20 210/635 |

OTHER PUBLICATIONS

Wikipedia reference (2016) regarding triangle apex.*
V. Sridar, "Rate acceleration of Fischer-indole cyclization by microwave irradiation," *Indian Journal of Chemistry Section B-Organic Chemistry Including Medicinal Chemistry* 36, 86-87 (1997).
"Technology Vision 2020," (The U.S. Chemical Industry, 1996).
V. Sridar, "Microwave radiation as a catalyst for chemical reactions," *Current Science* 74, 446-450 (1998).
C. O. Kappe, "High-speed combinatorial synthesis utilizing microwave irradiation," *Current Opinion in Chemical Biology* 6, 314-320 (2002).
D. Adam, "Microwave chemistry: Out of the kitchen," *Nature* 421, 571-572 (2003).
K. Aslan, S. N. Malyn, and C. D. Geddes, "Multicolor Microwave-Triggered Metal-Enhanced Chemiluminescence," *J. Am. Chem. Soc.* 128, 13372-13373 (2006).
R. S. Varma, "Solvent-free organic syntheses—using supported reagents and microwave irradiation," *Green Chemistry* 1, 43-55 (1999).
I. Roy, and M. N. Gupta, "Applications of microwaves in biological sciences," *Current Science* 85, 1685-1693 (2003).
R. Gedye, F. Smith, K. Westaway, H. Ali, L. Baldisera, L. Laberge, and J. Rousell, "The Use of Microwave-Ovens for Rapid Organic-Synthesis," *Tetrahedron Letters* 27, 279-282 (1986).
S. Jain, S. Sharma, and M. N. Gupta, "A microassay for protein determination using microwaves," *Analytical Biochemistry* 311, 84-86 (2002).
A. G. Whittaker, and D. M. P. Mingos, "Microwave-assisted solid-state reactions involving metal powders," *J. Chem. Soc. Dalton Trans.* 12, 2073-2079 (1995).
S. Caddick, "Microwave assisted organic reactions," *Tetrahedron* 51, 10403-10432 (1995).
M. Pagnotta, C. L. F. Pooley, B. Gurland, and M. Choi, "Microwave Activation of the Mutarotation of alpha-D-glucose—an Example of an Intrinsic Microwave Effect," *Journal of Physical Organic Chemistry* 6, 407-411 (1993).
A. B. Copty, Y. Neve-Oz, I. Barak, M. Golosovsky, and D. Davidov, "Evidence for a specific microwave radiation effect on the green fluorescent protein," *Biophysical Journal* 91, 1413-1423 (2006).
A. Shaman, S. Mizrahi, U. Cogan, and E. Shimoni, "Examining for possible non-thermal effects during heating in a microwave oven," *Food Chemistry* 103, 444-453 (2007).
R. K. Adair, "Biophysical limits on athermal effects of RF and microwave radiation," *Bioelectromagnetics* 24, 39-48 (2003).
K. R. Foster, "Thermal and nonthermal mechanisms of interaction of radio-frequency energy with biological systems," *Ieee Transactions on Plasma Science* 28, 15-23 (2000).
R. Weissenborn, K. Diederichs, W. Welte, G. Maret, and T. Gisler, "Non-thermal microwave effects on protein dynamics? An X-ray diffraction study on tetragonal lysozyme crystals," *Acta Crystallographica Section D-Biological Crystallography* 61, 163-172 (2005).
H. Bohr, and J. Bohr, "Microwave-enhanced folding and denaturation of globular proteins," *Physical Review E* 61, 4310-4314 (2000).
J. Gellermann, W. Wlodarczyk, B. Hildebrandt, H. Ganter, A. Nicolau, B. Rau, W. Tilly, H. Fahling, J. Nadobny, R. Felix, and P. Wust, "Noninvasive magnetic resonance thermography of recurrent rectal carcinoma in a 1.5 Tesla hybrid system," *Cancer Research* 65, 5872-5880 (2005).
K. Hamad-Schifferli, J. J. Schwartz, A. T. Santos, S. G. Zhang, and J. M. Jacobson, "Remote electronic control of DNA hybridization through inductive coupling to an attached metal nanocrystal antenna," *Nature* 415, 152-155 (2002).
M. J. R. Previte, and C. D. Geddes, "Spatial and Temporal Control of Microwave Triggered Chemiluminescence: A Rapid and Sensitive Small Molecule Detection Platform," *Analytical Chemistry* in preparation (2007).
C. L. R. Catherall, T. F. Palmer, and R. B. Cundall, "Chemiluminescence from Reactions of Bis(Pentachlorophenyl)Oxalate, Hydrogen-Peroxide and Fluorescent Compounds—Kinetics and Mechanism," *Journal of the Chemical Society-Faraday Transactions Ii* 80, 823-836 (1984).
O. Filevich, and R. Etchenique, "1D and 2D temperature imaging with a fluorescent ruthenium complex," *Analytical Chemistry* 78, 7499-7503 (2006).
B. Durham, J. V. Caspar, J. K. Nagle, and T. J. Meyer, "Photochemistry of Ru(bpy)$_3^{2+}$," *Journal of the American Chemical Society* 104, 4803-4810 (1982).
J. Vanhouten, and R. J. Watts, "Temperature-dependence of Photophysical and Photochemical Properties of Tris(2,2'-bypridyl)Ruthenium(II) Ion in Aqueous Solution," *Journal of the American Chemical Society* 98, 4853-4858 (1976).
M. J. R. Previte, and C. D. Geddes, "Microwave-triggered chemiluminescence with planar geometrical aluminum substrates: Theory, simulation and experiment," *Journal of Fluorescence* 17, 279-287 (2007).

* cited by examiner

FLUORESCENCE MICROSCOPE IN MICROWAVE CAVITY

CROSS REFERENCE TO RELATED APPLICATION

The present application is a divisional application of and claims priority to copending U.S. patent application Ser. No. 12/602,552 filed on May 6, 2010, now U.S. Pat. No. 8,404,450, which was an filed under the provisions of 35 U.S.C. §371 and claimed priority to International Patent Application No. PCT/US2008/065801 filed on Jun. 4, 2008, which in turn claimed priority of U.S. Provisional Application No. 60/932,620 filed on Jun. 4, 2007, the contents of all which are incorporated by reference herein for all purposes.

BACKGROUND OF THE INVENTION

Technical Field

The present invention relates to an optical imaging system, and more particularly to the use of electromagnetic energy in the microwave or radiofrequency range in combination with an optical imaging device for imaging real time luminescent reactions.

Related Art

Optical microscopy is a well-established technique that has wide ranging applications for imaging molecular dynamics of biological systems. Typically, these applications rely on external temperature controllers to maintain or change reactions rates of these biological systems. While microwaves have been shown to accelerate the rate of chemical reactions[1-7] and enzyme-catalyzed biological reactions [6, 8-11] some argue that the enhanced reaction rates in many microwave assisted reactions cannot be explained by heating alone. It has been suggested that there exists a "non-thermal" effect on biological systems, which potentially permutes enzyme, DNA and protein function and conformation after microwave exposure [6,12-16]. Recent works summarize some existing theories with regard to the interactions of microwaves with biological systems [17-19]. However, heretofore, the systems available could only look at the conditions before the reactions and then take another look after completion of the reactions [15, 20-22].

More recently, Copty, et al. published work that studied microwave effects on green fluorescent protein (GFP) in real-time and compared same to normal thermal heating [15]. However, the system used by Copty did not provide sufficient visibility of structures or the ability to measure physiological and biochemical event in living cells.

To perform related studies and address the need for real-time data of microwave effects on biological processes, a real-time imaging system having increase resolution would greatly facilitate the understanding of microwave effects on enzyme reactions rates, biomolecular interactions, and living biological organisms, i.e. mammalian cells. Thus, there is a need for using microwave focused and triggering technologies to capture real-time images of microwave induced solution heating and accelerated chemical reactions to analyze interactions of biomolecules in vitro and in vivo.

SUMMARY OF THE INVENTION

The present invention relates to an optical imaging system that provides for increases in chemical reaction times and the ability to monitor the reactions in real time with sufficient resolution to view the location of intracellular components labeled with luminescent molecules, as well as, interaction between multiple biomolecules and responses to localized environmental variables in living cells and tissues.

In one aspect the present invention relates to a microwave/optical imaging system comprising:
  a) an enclosed container comprising a microwave cavity and having at least one opening therein;
  b) a sample plate positioned within the microwave cavity for holding at least one sample, wherein the sample comprises a detector molecule or components of a detectable reaction;
  c) a microwave energy producing source communicatively connected to the microwave cavity for delivering microwave energy into the cavity and directed towards the sample;
  d) an electromagnetic energy producing source positioned for delivering energy to the sample; and
  e) an optical imaging device communicatively connected to the microwave cavity and positioned for directing light from the electromagnetic energy producing source to the sample and capturing luminescent emissions emitted from the sample.

In another aspect, the present invention relates to a microwave/microscope system, the system comprising:
  a) an enclosed container comprising a microwave cavity and a predetermined-sized opening therein, wherein the interior of the microwave cavity includes a stage for positioning at least one sample plate for holding at least one sample, wherein the sample comprises a signal producing agent included as an additional tag molecule or formed agent due to chemical reaction in the sample;
  b) a microwave energy producing source communicatively connected to the microwave cavity for delivering microwave energy into the cavity; and
  c) a fluorescence microscope system communicatively connected to the microwave cavity and positioned for delivering excitation energy to the sample and capturing emissions from the sample, wherein the fluorescence microscope system comprises:
    an electromagnetic energy producing source to produce energy at a frequency to excite the sample;
    an objective positioned for receiving electromagnetic energy from the source and focusing same on the sample;
    a dichroic mirror positioned between the laser and objective for reflecting electromagnetic energy from the energy source to the objective and for directing emitted signals from the sample; and
    a tube lens positioned after the dichroic mirror for collecting emissions from the sample and directing same to a detector device.

The sample plate may comprise at least one layer of metallic material deposited on the sample plate surface including silver, gold, copper, zinc, aluminum, or platinum wherein the metallic material is formed into a patterned shape. Preferably, the patterned shape includes geometric shapes having at least one apex, such as, a triangle, square, rectangle, trapezoid, polygon, parabola, elliptical, a sector of a circle, oblong and/or combinations thereof, wherein the numerous apexes are adjacent to each other, thereby creating a reactive zone therebetween. The reactive zone therebetween may further be prepared for placement of the immobilized capture molecule complementary to a detector molecule, chemicals for reacting with other chemicals, or biomolecules for reacting with other biomolecules. The reactive zone may have a diameter or distance between the adjacent and/or opposing apexes ranging from about 0.01 mm to 5 mm, and more preferably from about 2 mm to 3 mm. Further, the reactive zone can be positioned on assay system with multiple wells wherein the reactive zone is within the wells and exposure to microwave energy enhances the reactions therein.

The sample plate may be fabricated of a polymeric material, glass, paper, nitrocellulose, combinations thereof or any material that provides sufficient stability for placement of the metallic material.

The apex area/reactive zone is exposed to microwave energy in an amount to increase the reaction rate in biological interactions, to increase intensity of emissions from the chemiluminescence reaction, fluorescence, phosphorescence or luminescence tags in sensing technologies; to enhance electric fields by focusing electromagnetic fields in the reactive zone and/or to increase Brownian motion in molecules contained within the reactive zone.

Another aspect of the present invention relates to a method for preparing a sample plate the method comprising;
a) applying at least one metallic structure to a substrate surface including but not limited to glass, polymeric, paper, nitrocellulose, wherein the metallic structure is fabricated of silver, gold, aluminum, zinc, platinum, copper or combinations thereof, wherein the metallic structures are in a formed pattern, and wherein an area of the formed pattern includes an apex area which is positioned near the apex of another formed pattern, thereby providing a reactive zone positioned between at least two apex areas; and
b) introducing a solution containing at least one biomolecule for disposing in the reactive zone between the adjacent apex areas.

Another aspect of the present invention relates to a method of imaging real-time data of microwave induced reactions or interactions of biomolecules, the method comprising:
a) providing a sample comprising at least one biomolecule and a detector molecule, wherein the sample is positioned on a sample plate;
b) placing the sample in a microwave cavity, wherein the microwave cavity is communicatively connected to a microwave producing source and also communicatively connected to an optical imaging system, wherein the optical imaging system comprises:
 i. an electromagnetic energy producing source to produce energy at a frequency to excite the sample;
 ii. an objective positioned for receiving excitation electromagnetic energy and focusing same on the sample;
 iii. a dichroic mirror positioned between the laser and objective for reflecting electromagnetic energy from the energy source to the objective and for directing emitted signals from the sample; and
 iv. a tube lens positioned after the dichroic mirror for collecting emissions from the sample and directing same to a detector device
c) irradiating the sample with low power microwave energy in an amount to increase interactions or reactions in the sample; and
d) imaging the emission signal of the detector molecule with the optical imaging system of step b).

The use of low power microwave energy directed at the sample that is positioned in a reactive zone formed by adjacent metallic patterns increases the speed of chemical reactions occurring within the sample.

Other features and advantages of the invention will be apparent from the following detailed description, drawings and claims.

during the application of the microwave pulse and D) maximum 'triggered' emission E) final emission.

Figure 10:
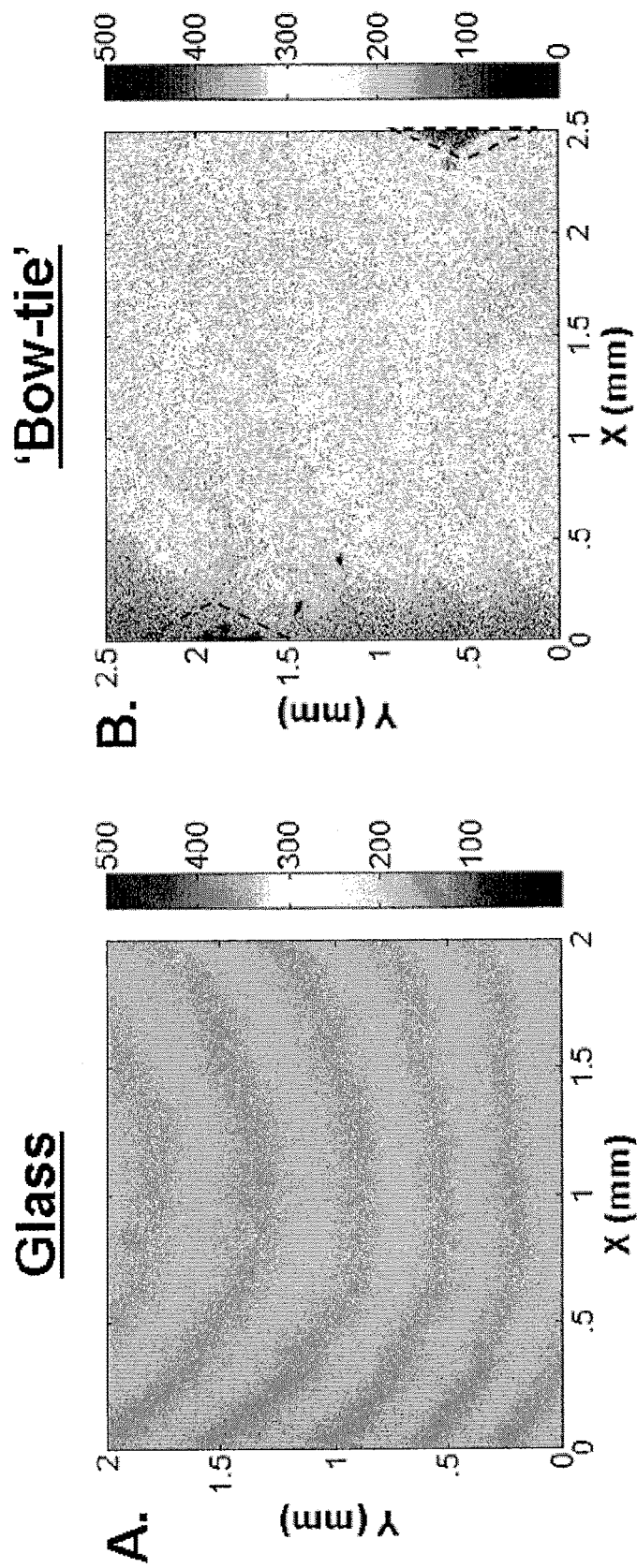

FIG. 10 shows CCD movie images for green for 6 μl of chemiluminescence solution A) on glass substrates and in the gap of B) disjointed 'bow-tie' geometries (dashed outline denote triangle 'bow-tie' tips.

DETAILED DESCRIPTION OF THE INVENTION

The present invention relates to a real-time optical imaging system communicatively connected to a microwave energy producing source thereby providing means to record real-time data of biomolecule interactions and reactions in biological systems during the application of a microwave field.

The system of the present invention can provide for real-time imaging microwave or radiofrequency driven interaction between protein-protein, DNA-protein, RNA-Protein, DNA-RNA, chemical-protein, chemical-DNA, and chemical-protein interactions at surfaces, in solution, in living organisms, including prokaryotes and eukaryotes. Further, the present invention provides for real-time imaging of microwave induced effects on biological systems, induced biomolecular reactions in prokaryotic and eukaryotic organisms, at interfaces, surfaces and in solutions. Still further, the present invention provides for real-time imaging of microwave induced transfection of small biomolecules into living organisms, prokaryotes and eukaryotes.

The term "biomolecule" as used herein means any molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, proteins, peptides, carbohydrates, steroids, flavins, DNA, RNA, oligonucleotides, nucleic acids, fatty acids, myoglobin, sugar groups such as glucose etc., vitamins, cofactors, purines, pyrimidines, formycin, lipids, phytochrome, phytofluor, peptides, lipids, antibodies and phycobiliproptein.

The term "receptor-ligand" as used herein means any naturally occurring or unnaturally occurring binding couple wherein the components have affinity for each other. For example, the binding couple may include an antibody/antigen complex, viral coat ligand/protein cell receptor or any combination of probe and binding partner. The term "receptor" refers to a chemical group, molecule, biological agent, naturally occurring or synthetic that has an affinity for a specific chemical group, molecule, virus, probe or any biological agent target in a sample. The choice of a receptor-ligand for use in the present invention will be determined by nature of the disease, condition, or infection to be assayed.

The system of the present invention includes a detector molecule or a detectable chemical reaction that is responsive to electromagnetic excitation, chemical excitation, excitation by a light source, or a laser beam of continuous or pulsed excitation to produce luminescence, including chemiluminescence, fluorescence, or phosphorescence emissions.

Detector molecules include fluorophores that emit electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY®, naphthalamine sulfonic acids including but not limited to 1-anilinonaphthalene-8-sulfonic acid (ANS) and 6-(p-toluidinyl) naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 lodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Any chemiluminescent species may be used in the present invention that provides for a chemical reaction which produces a detectable reaction (observed emission) wherein the excited state responsible for the observed emission including, but not limited to the following excitation mechanisms:

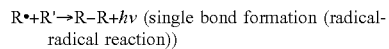
R•+R'•→R–R+hv (single bond formation (radical-radical reaction))

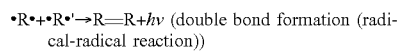
•R•+•R•'→R═R+hv (double bond formation (radical-radical reaction))

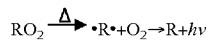
$RO_2 \xrightarrow{\Delta}$ •R+$O_2$→R+hv

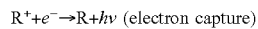
$R^+$+$e^-$→R+hv (electron capture)

Examples of suitable chemiluminescence detector molecules include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, a Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen. Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio) proprionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

Figure 1:
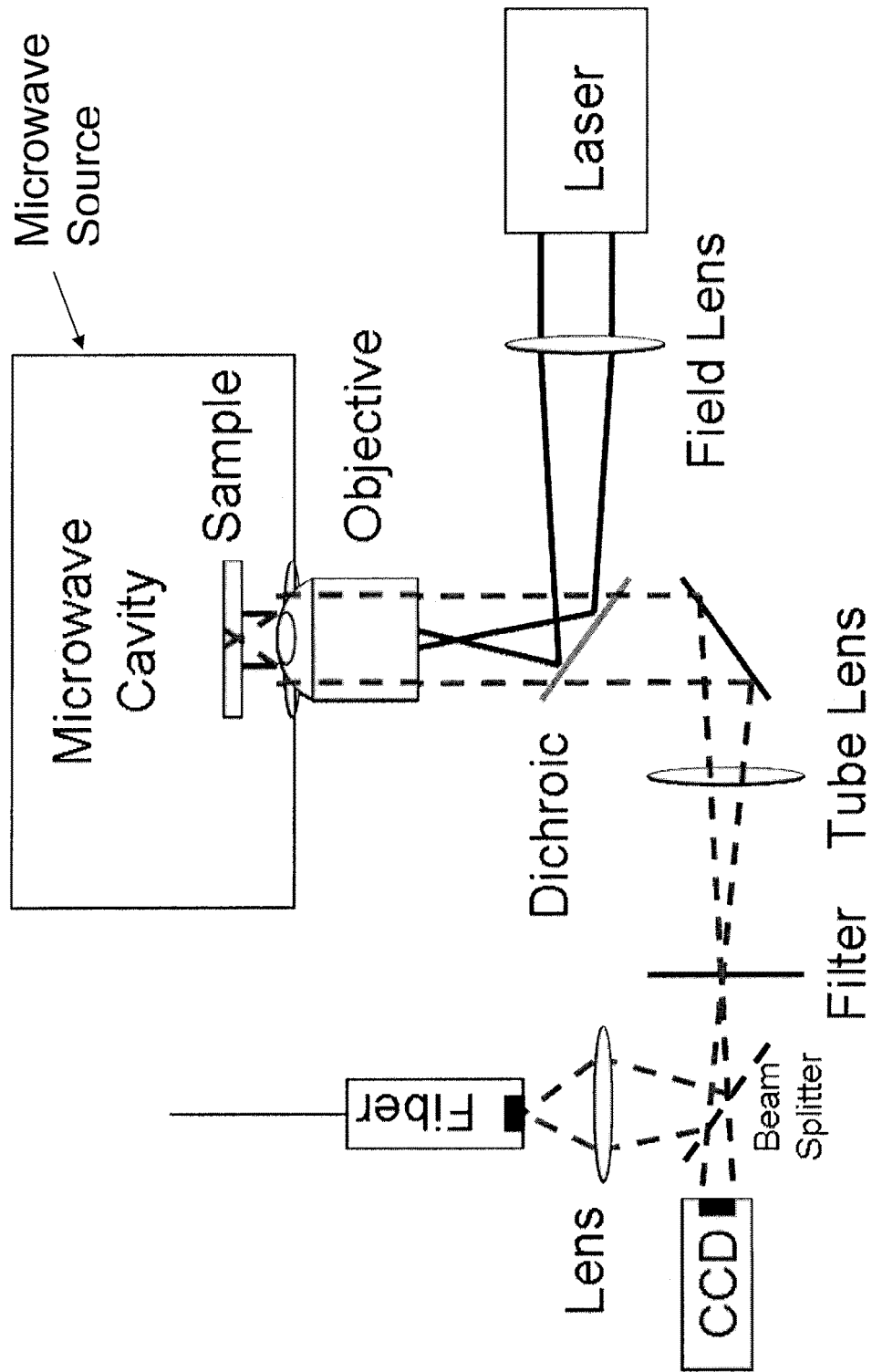
FIG. 1 shows an embodiment of the microwave/microscope of the present invention.

Generally, any combination of optical imaging systems and microwave based technologies may be used in the present invention. As shown in FIG. 1 the system includes a microwave cavity for placement of a sample and a source for generating electromagnetic energy having a wavelength and frequency in a microwave or radiofrequency range, and more preferably in the microwave range.

The application of low level microwave energy for heating of the sample may be used to speed up any biological/biochemical kinetics within the system. Notably, low level microwaves do not destroy or denature proteins, DNA, or RNA, but instead heat the sample sufficiently to provide for accelerated kinetics such as binding, hybridization or chemical interaction.

Microwaves (about 0.3 to about 300 GHz) lie between the infrared and radio frequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, where as microwaves are effectively transparent to hexane, toluene and diethylether.

In the present invention, microwave radiation may be provided by an electromagnetic source having a frequency in a range between 0.3 and 10 GHz, more preferably from about 1 GHz and 5 GHz, and more preferably from 2 GHz to 3, and a power level in a range between about 10 mwatts and 700 watts, preferably from 30 mwatts to about 500 watts, and more preferably from about 50 watts to 300 watts. Any source, known to one skilled in the art may be used, such as a laser having the capacity to emit energy in the microwave range. The microwave radiation may be emitted continuously or intermittently (pulsed), as desired.

In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

In one embodiment, a sample plate is modified by adhering metallic surfaces fabricated to form a geometric shape such as triangle, square, oblong, elliptical, rectangle, or any shape that provides at least one apex area of the metallic surface. Further multiple metallic geometric shapes may be adhered to a surface in the form of a pattern to provide at least one reactive zone positioned between the apex areas. It is envisioned that the apex area includes not only pointed regions but regions with rounded edges such as found in an oblong or elliptical shape. The apex areas are preferably arranged so that one apex area is opposite from another apex area and aligned to cause the reactive zone to be positioned therebetween. The distances between the apex areas may range from 0.01 mm to 5 mm, more preferably from 2 mm to about 3 mm and depending on the size of the required reactive zone. The thickness of the metallic geometric shaped forms ranges from 25 nm to about 1000 nm, and more preferably from about 45 nm to about 250 nm.

The geometric shapes can be formed on the surface substrate by any means known to those skilled in the art, including masking the surface substrate with subsequent deposition of the metallic material, fixing preformed metallic geometric shapes directly onto the substrate surface, or impregnating a geometric shaped recess in the surface substrate with a metallic material that provides for a continuous planar surface on the substrate. Further, the geometric shapes may include a diversity of material including dielectric materials. For example a layer of metallic material can be deposited on a substrate surface with a layer of $SiO_2$ deposited thereon.

In another embodiment, the present invention provides enhanced emissions using metalized islands of elliptical, spherical, triangular or rod-like forms. Further, the metallic material may be in the form of a porous three dimensional matrix. The three dimensional matrix may be a nano-porous three dimensional matrix. The metallic material may include metal colloid particles and or shaped particles imbedded into the surface of a glass of polymeric polymer matrix.

As further shown in FIG. 1, the system includes a source of electromagnetic energy, communicatively connected to the cavity to transmit irradiating energy to the sample and detector material thereby inducing chemical excitation, electrical excitation, or single or multiphoton excitation to produce characteristic luminescence in the detector material. Notably, the source used for applying electromagnetic energy can include any device that applies the necessary frequency or wavelength such as arc lamps, including mercury or xenon; laser diode and LED sources having the ability to generate single or multiple photons in a continuous or pulsing modes, wherein the intensity of said electromagnetic energy corresponds to absorption and subsequent luminescence of said detector molecule or detectable reaction. Laser commonly employed are high-intensity monochromatic light sources, however, it should be noted that multiple point lasers are also envisioned.

In another embodiment, using 2-photon excitation at 700-1000 nm and also using short pulse width (<50 pi), high repetition rate (1-80 MHz), laser diode and LED (1 ns, 1-10 MHz) sources provide enhanced sensitivity as compared to 1-photon excitation. If a fluorophore absorbs two photons simultaneously, it will absorb enough energy to be raised to an excited state. The fluorophore will then emit a single photon with a wavelength that depends on the fluorophore used and typically in the visible spectra.

The optical imaging/microwave system of the present invention includes not only the light source discussed herein above but also the optics needed to observe the emitted excitation signal, such as fluorescence. The light source emit lights, likely in the ultraviolet range and hits a dichroic mirror that reflects one range of wavelengths and allows another range to pass through. The dichroic mirror reflects the light to the sample for excitation of fluorescence within molecules in the sample and/or detector molecules. An objective lens collects the fluorescent-wavelength light produced. This fluorescent light passes through the dichroic mirror, and preferably a filter that eliminates wavelengths other than fluorescent, making it to the imaging device. Preferably, the fluorescence microscope uses an epifluorescence setup wherein the objective lens is used both to focus the irradiating light onto the sample/detector molecule and also collect the fluorescent light emitted from the sample/detector molecule.

The structure comprising the microwave cavity is constructed for connectivity to the optical imaging system wherein an opening is fabricated in the cavity for directing the focused light onto the sample and for existing of emitted fluorescent wavelength light. The light source generates a beam of light directed into the objective and preferably the beam of light is passed through a beam expander lens for expansion of the light beam sufficient to provide an expanded beam of excitation light entering into the cavity for focusing on the sample.

Excited emissions existing the cavity and through the objective can be detected using an optical detector. Various optical detectors, such as photodiode, charge-coupled device (CCD), photomultiplier tube (PMT), or photon counting detector, may be used wherein each has a different degrees of sensitivity. PMT and photon counting detectors can achieve an electronic amplification factor as high as $10^6$-$10^8$. Conventional PMTs require a ~1 kV power source, but new miniaturized detector requires only a 5 V. Most of the chemiluminescence emission wavelengths are in the visible region. A narrow-band optical filter may be used to ensure detecting luminescence wavelengths. The system may further include a microactuator, detector, microprocessor, electronics, a display, and translation stage. The output of the detector may be interfaced to an analog to digital converter and a microprocessor to calculate analyte concentration.

Further, the system of the present invention may include a sample platform that is movable in xy and z directions. Additionally, the use of a multi-point laser is considered for generating an array of point excitation directed to the objective for focusing on the sample, thereby creating an array of multiple focused spots. Still further, the system can include means for adjusting lenses in the system to select focal points at different depths within the sample to impinge upon the detector molecule or detectable reaction at the object plane. Notably, the systems can include a combination of components for delivering simultaneous or sequential spatially and/or temporally controlled electromagnetic radiation to control the activity of biological or chemical reactions that directly or indirectly relates to any small biomolecule, chemical molecule, any sized or collection of particles composed of any dielectric material, including any nanoparticles or carbon nanotubes, prokaryotic organism, eukaryotic organism and/or combination thereof.

Still further, the combined optical imaging and microwave system of the present invention may include an optical imaging system including but not limited to fluorescence, luminescence, wide-field, confocal reflected, confocal, two-photon, multiphoton, wide-field, spinning disk, Nipkow spinning disk, 4-pi confocal, fluorescence resonance energy transfer (FRET) for imaging molecular interactions, total internal reflection fluorescence microscopy (TIRFM) for imaging interactions of molecules with surfaces, multi-foci, multi-foci multiphoton, near-field, single molecule, spectral imaging, lifetime imaging, fluorescence imaging, fluorescence correlation spectroscopy, raster imaging correlation spectroscopy (RICS), and image correlation spectroscopy (ICS).

Examples

Methods and Materials

Premium quality APS-coated glass slides (75×25 mm) were obtained from Sigma-Aldrich. CoverWell imaging chamber gaskets with adhesive (2.5 mm diameter, 2 mm deep and 5 mm diameter, 2 mm deep for temperature measurements) were obtained from Molecular Probes (Eugene, Oreg.). $Ru(by)_2Cl_2$ salt was obtained from Sigma-Aldrich. Commercially available chemiluminescence materials were purchased from Unique Industries, Inc.

Optical Set-Up of Wide Field Microscope in Microwave Cavity

At the base of a microwave cavity (0.7 cu ft, GE Compact Microwave Model: JES735BF, max power 700 W), a 1 inch hole was drilled and subsequent exposed metal surfaces were covered with white enamel paint to prevent sparking and arcing. Using a beam expander the spot size of a 473 nm laser source was expanded to approximately 1 inch and focused to a point with a 175 mm lens at the back aperture of the objective. The incident excitation beam was reflected with a dichroic mirror (z479/532rpc, Chroma, Brattleboro, Vt.) into an infinity corrected brightfield objective (LWD Plan Achromat objective –LPL10×objective/NA=0.25). The fluorescent emission intensity, which is generated by wide-field excitation working in epifluorescence mode, is collected through the infinity corrected optics and imaged onto a CCD camera using a razor edge 488 nm and a 570 LP filter to block any bleedthrough of the excitation light as shown in FIG. 1. Chemiluminescence intensity images are imaged through the infinity corrected optics and imaged onto a CCD camera in the absence of any optical filters. CCD images were taken with a Retiga-SRV CCD Camera (QImaging, Burnaby, B.C.) with 4×4 binning at 10 fps. Emission spectra were collected using an Ocean Optics spectrometer, model SD 2000 (Dunedin, Fla.) that is connected to an Ocean Optics 1000 μm diameter fiber with a NA of 0.22 (Dunedin, Fla.). A collimator is connected to the end of the fiber and positioned to maximize the coupling of the fluorescence emission into the spectrometer. $Ru(by)_2Cl_2$ time-dependent emission spectra were collected with an integration time of 100 milliseconds. All exposed metal surfaces of the objective and adaptive optics were coated with white reflective paint to prevent sparking and arcing during the application of microwave pulses.

Formation of Continuous Metal Films on APS-Coated Glass Substrates

Figure 2:
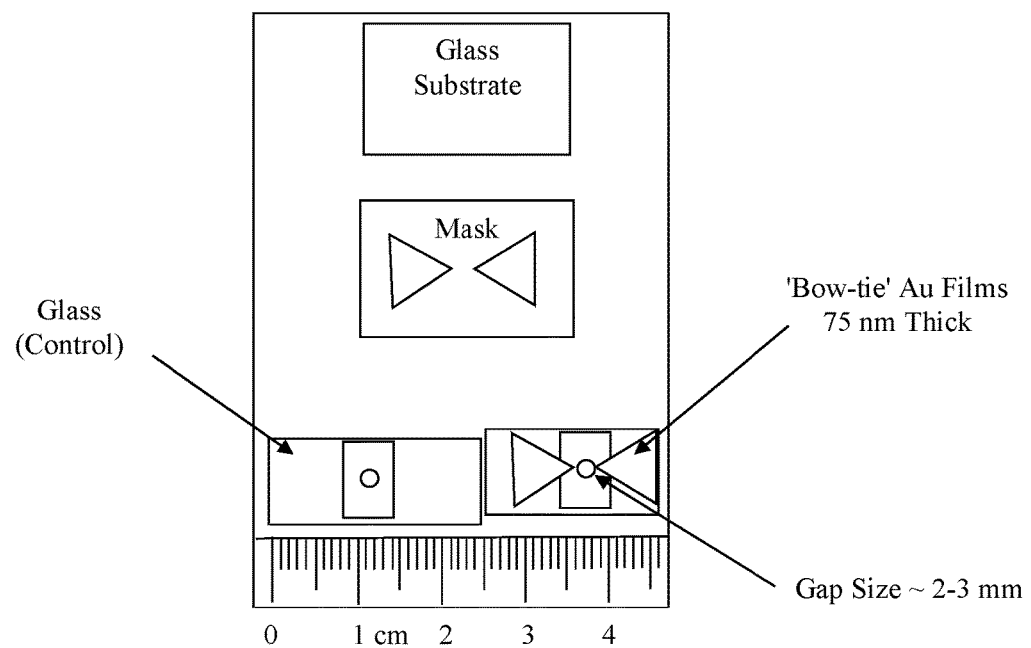
FIG. 2 shows the sample geometry scheme for preparing a sample plate for use in the herein described systems.

The preparation of glass slides modified with 'bow-tie' structures has been described previously [23]. Briefly, disjointed 'bow-tie' equilateral 2.5 mm triangles stencils were made from an adhesive mask. The disjointed 'bow-tie' structure was formed from two inverted 5 mm triangles, such that the distance between the apexes or gap size was approximately 2-3 mm, as shown in FIG. 2. Triangle tape masks were affixed to plain glass slides and glass slides modified with Ag triangle structures were created by vapor depositing 75 nm of Au films on glass using an EMF Corp. (Ithaca, N.Y.) vapor deposition instrument. Film thicknesses were monitored during the deposition process with an Edwards FTM6 film thickness monitor.

Sample Preparation

Glass substrates with and without modified 'bowtie' metal structures were cut into 10×10 mm sample sizes. Image wells were placed between the two vapor deposited Au triangles 75 nm thick or at the 'bowtie' gap and on the unmodified plain glass substrates. The samples were subsequently filled with 20 µl of 10 µM $Ru(by)_2Cl_2$ solution or 6 µl of chemiluminescence material (FIG. 2.).

Chemiluminescence Reagents (Chemical Reaction Assays)

The commercially available glow-sticks contain a phenyl oxalate ester, a fluorescent probe and a glass capsule containing the activating agent (hydrogen peroxide). Activation of the chemicals is accomplished by breaking an encapsulated glass capsule that contains the peroxide and subsequently mixes the chemicals to begin the chemiluminescence reaction. The hydrogen peroxide oxidizes the phenyl oxalate ester to a peroxyacid ester and phenol [24]. The unstable peroxyacid ester decomposes to a peroxy compound and phenol, the process chemically inducing an electronic excited state [24].

$Ru(by)_2Cl_2$ Temperature Measurements

Previously, ruthenium chloride aqueous solutions have been used to calibrate a temperature imaging system with a CCD sensor [25]. It is known that the emission intensity of these solutions decrease with temperature. The temperature dependence of the photophysical and photochemical properties of ruthenium chloride aqueous solutions have been described in detail elsewhere [26, 27]. Subsequently, a pre-calibrated intensity vs. temperature plot of a 10 µM aqueous solutions of $Ru(by)_2Cl_2$ was recorded using a Cary Eclipse fluorescence spectrometer with temperature controller. Calibration temperatures were 10, 20, 30, 40, 50, 60, and 70° C., which is within the linear range of the relationship between the relative fluorescence to the temperature, as shown in FIG. 3.

Figure 3:
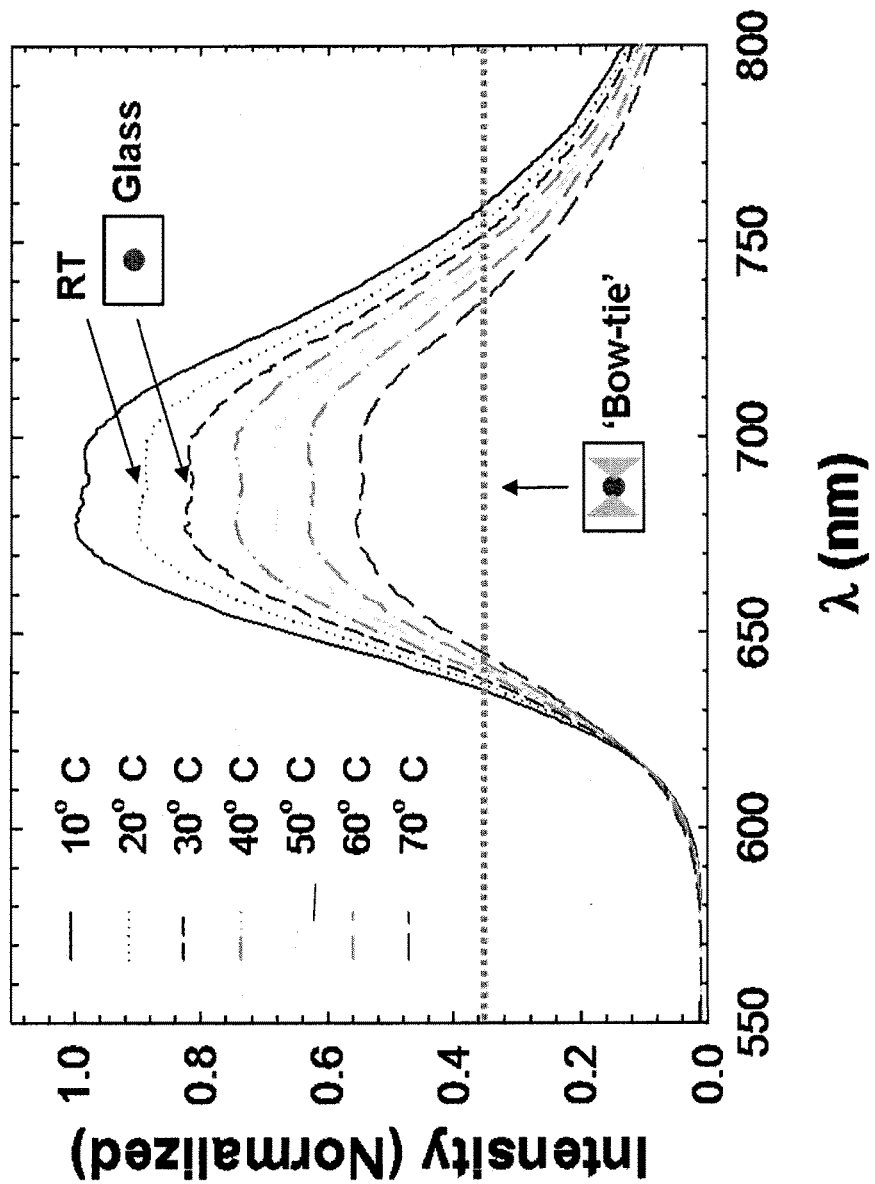
FIG. 3 shows normalized intensity spectra for 10 µM $Ru(by)_2Cl_2$ at different temperatures. Normalized intensity ratios of 10 µM $Ru(by)_2Cl_2$ solutions are marked with an arrow for the glass geometry (inset, sample geometry) and a dotted line for the 'bow-tie' sample geometries (inset, sample geometry). Normalized intensity ratios are calculated as the ratio of the time dependent emission intensity during to the maximum emission intensity before exposure to short microwave pulse.

For the microwave imaging experiments, the intensity of fluorescence emission was measured from 10 µM aqueous solutions of $Ru(by)_2Cl_2$ on glass substrates in the presence and absence of the thin continuous metal film triangle geometries 75 nm thick (FIG. 3). $Ru(by)_2Cl_2$ aqueous solutions were excited with a 473 nm laser source. Before and during the application of a 5 second low power 2.45 GHz microwave pulses (10% power), the spectral emission from the $Ru(by)_2Cl_2$ aqueous solutions was recorded at 100 millisecond time intervals for 20 seconds using the fiber detection and spectrometer optical configuration of FIG. 1. The recorded fluorescence spectral intensity from the $Ru(by)_2Cl_2$ aqueous solutions on glass substrates and 'bow-tie' modified substrates before and during the application of the microwave pulse were normalized, as shown in FIG. 3.

Figure 4:
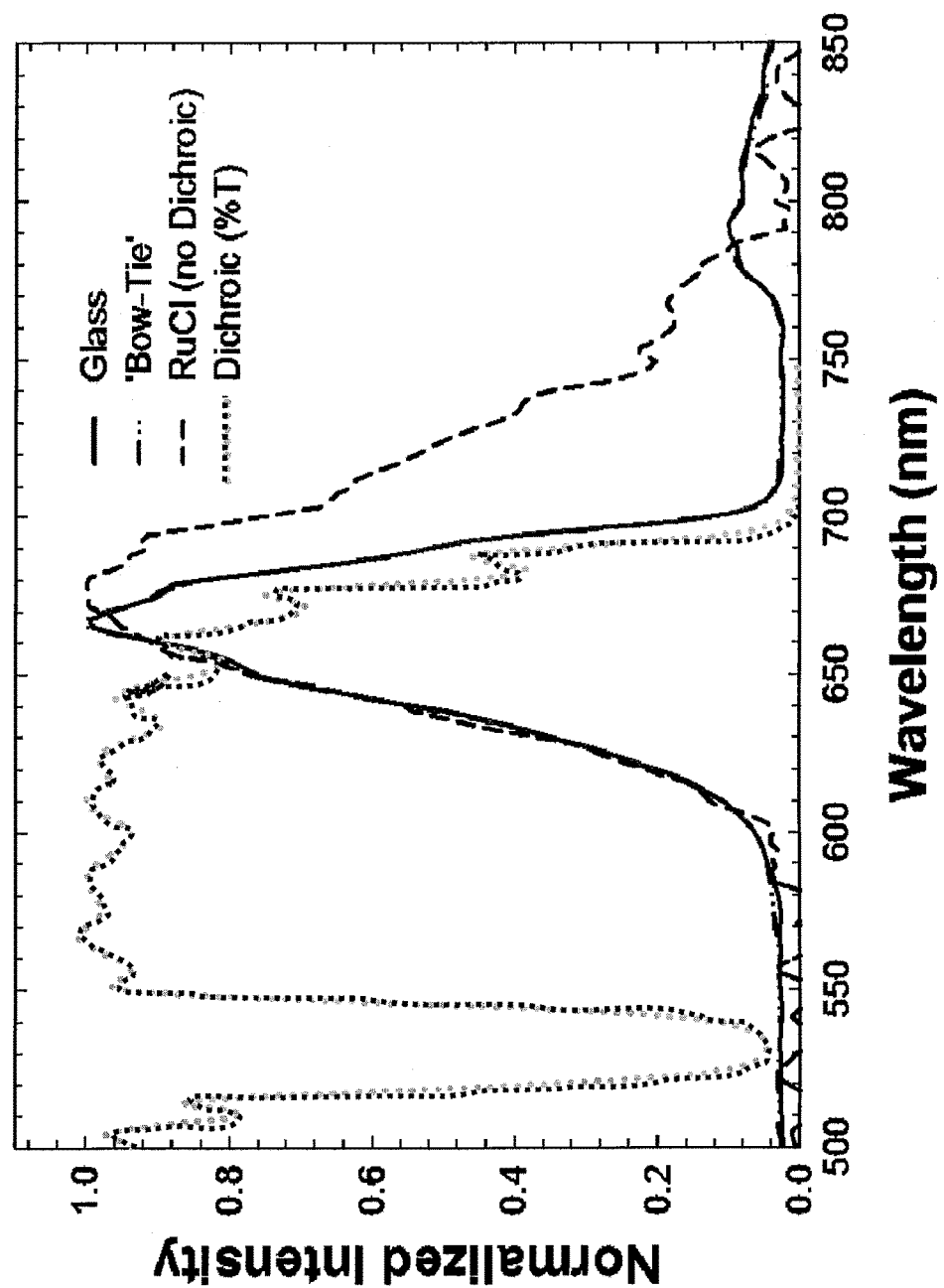
FIG. 4 shows the normalized spectra of $Ru(by)_2Cl_2$ emission (no dichroic) before (large dashed ━ ━ ) ) and during the application of low power microwave pulses for 'bow-tie'( ← ·· ━ ·· ) ) and glass slide ( ( ━ ) ) sample geometries. Dichroic transmission curve is overlaid to show the filtering effect of the dichroic on $Ru(by)_2Cl_2$ emission.

The normalized spectra are superimposed to determine if the microwave fields induce any spectral change to the $Ru(by)_2Cl_2$ emission, as shown in FIG. 4. The CCD time dependent intensities are normalized with respect to the maximum emission intensity (time=0). Normalized intensity ratios are calculated as the ratio of the time dependent emission intensity during to the maximum emission intensity before exposure to short microwave pulse. Subsequently, these ratios multiplied by a factor of 0.9 (FIG. 3, RT) to reflect the normalized intensity ratio for 10 µM aqueous solutions of $Ru(by)_2Cl_2$ at room temperature (FIG. 4). Subsequently, the corresponding temperature values for microwave heated solutions on glass substrates and substrates with 'bow-tie geometries could be approximated from the pre-calibrated intensity vs. temperature plot of a $Ru(by)_2Cl_2$ sample of the same concentration (FIG. 3, arrow and dashed line).

Total emission intensity images for $Ru(by)_2Cl_2$ aqueous solutions and chemiluminescence samples were captured at frame rate of 10 Hz using a CCD camera (FIGS. 6-10). In order to obtain the same initial chemiluminescence emission for all measurements, approximately 6 µl of the chemiluminescence solution was placed inside the imaging chamber. Data collection commenced 10 seconds prior to the application of the five second microwave pulse and continued until 20 seconds after microwave exposure.

Results and Discussion

Since it is well established that the emission intensity of $Ru(by)_2Cl_2$ solutions are inversely proportional to temperature, the emission spectra for $Ru(by)_2Cl_2$ solutions was recorded over a range of temperatures [28]. From these spectra, a linear relationship was observed between the emission intensity and temperature for the 10 µM $Ru(by)_2Cl_2$ solutions between 10° C. and 70° C., which is consistent with previously published results [23]. Using the fiber detection configuration of the optical scheme (FIG. 1), the fluorescence intensity was recorded from the $Ru(by)_2Cl_2$ aqueous solution at 100 millisecond time intervals for approximately 60 seconds. During the 60 second recording, we applied a five second 2.45 GHz pulse microwave pulse. Normalized intensity vs. temperature plots of the $Ru(by)_2Cl_2$ sample of the same concentration (FIG. 3) was fit to a linear function (data not shown). The approximate microwave induced maximum temperature increases to the solutions on the glass and 'bow-tie sample geometries are marked with an arrow and dashed line, respectively, as shown in FIG. 3.

Although only part of the $Ru(by)_2Cl_2$ spectra is transmitted in the presence of the dichroic, the superimposed normalized intensity spectra of the $Ru(by)_2Cl_2$ before the application of a microwave pulse is shown in FIG. 4. Typically, spectral shifts in chromophore emission are ascribed to the changes in the electronic distribution of the energies of electronic transitions [29]. Since the normalized intensity spectra of $Ru(by)_2Cl_2$ solutions before the application of a microwave pulse (FIG. 4, black line) is not permuted during the application of a low power microwave pulse (FIG. 4, dotted and dashed lines), it was concluded that the microwave heating does not create any noticeable change in the photophysical properties of the $Ru(by)_2Cl_2$ solutions [29].

Figure 5:
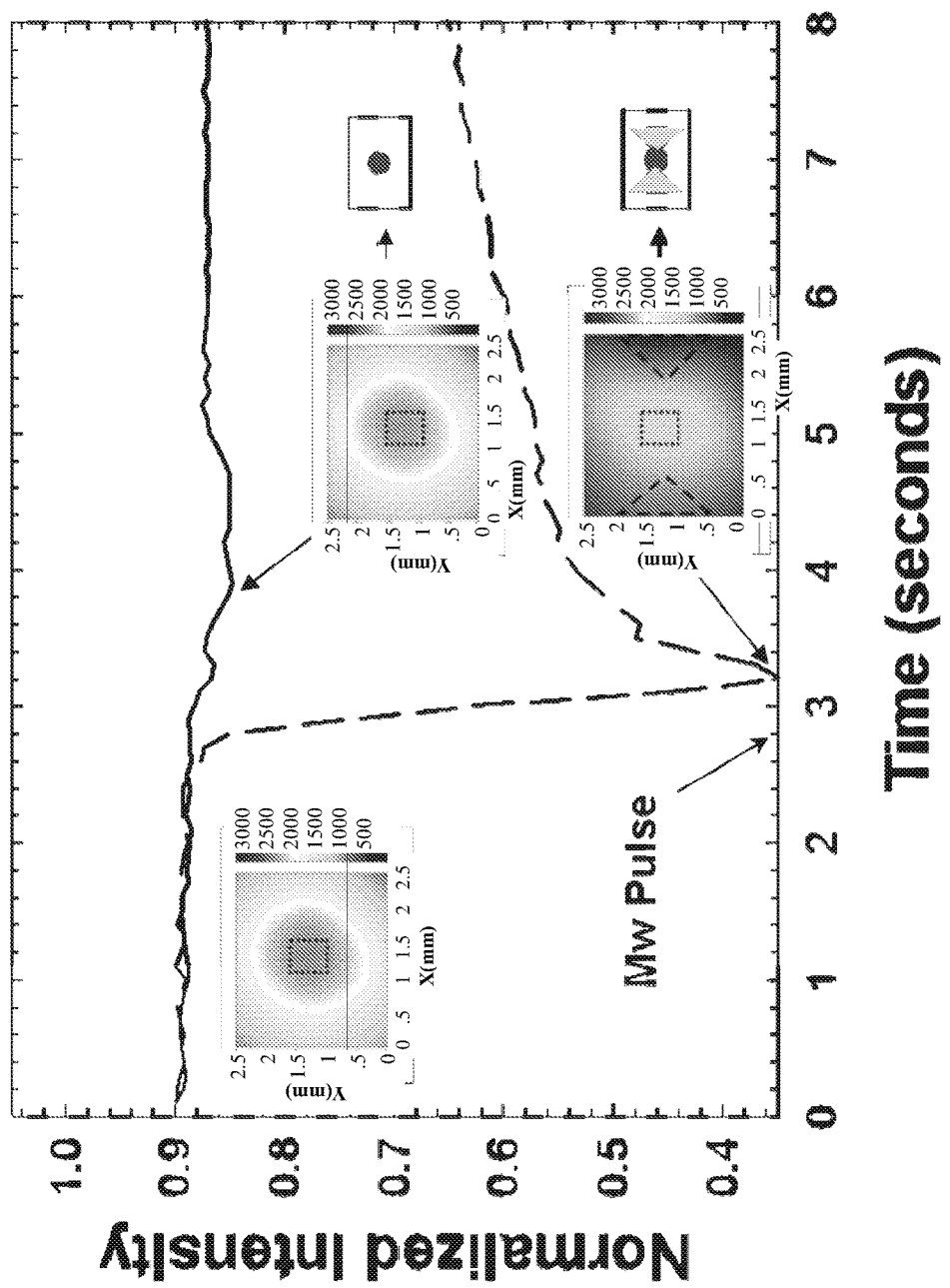
FIG. 5 shows the normalized average fluorescence intensity over 100 $pixel^2$ region (selected region approximated by box) time traces from CCD images for 10 µM $Ru(by)_2Cl_2$ solution at disjointed 'bow-tie' junction and on plain glass slides (control) during the application of 5 second low power microwave pulse (Mw pulse). Sample configurations are shown to the right of the CCD images. (insets)

Using the CCD imaging configuration, the fluorescence intensity images was recorded of the $Ru(by)_2Cl_2$ aqueous solutions on the glass substrates with and without 'bow-tie' structures in the microwave cavity at a frame rate of 10 Hz for 10 seconds (FIG. 5).

Figure 9:
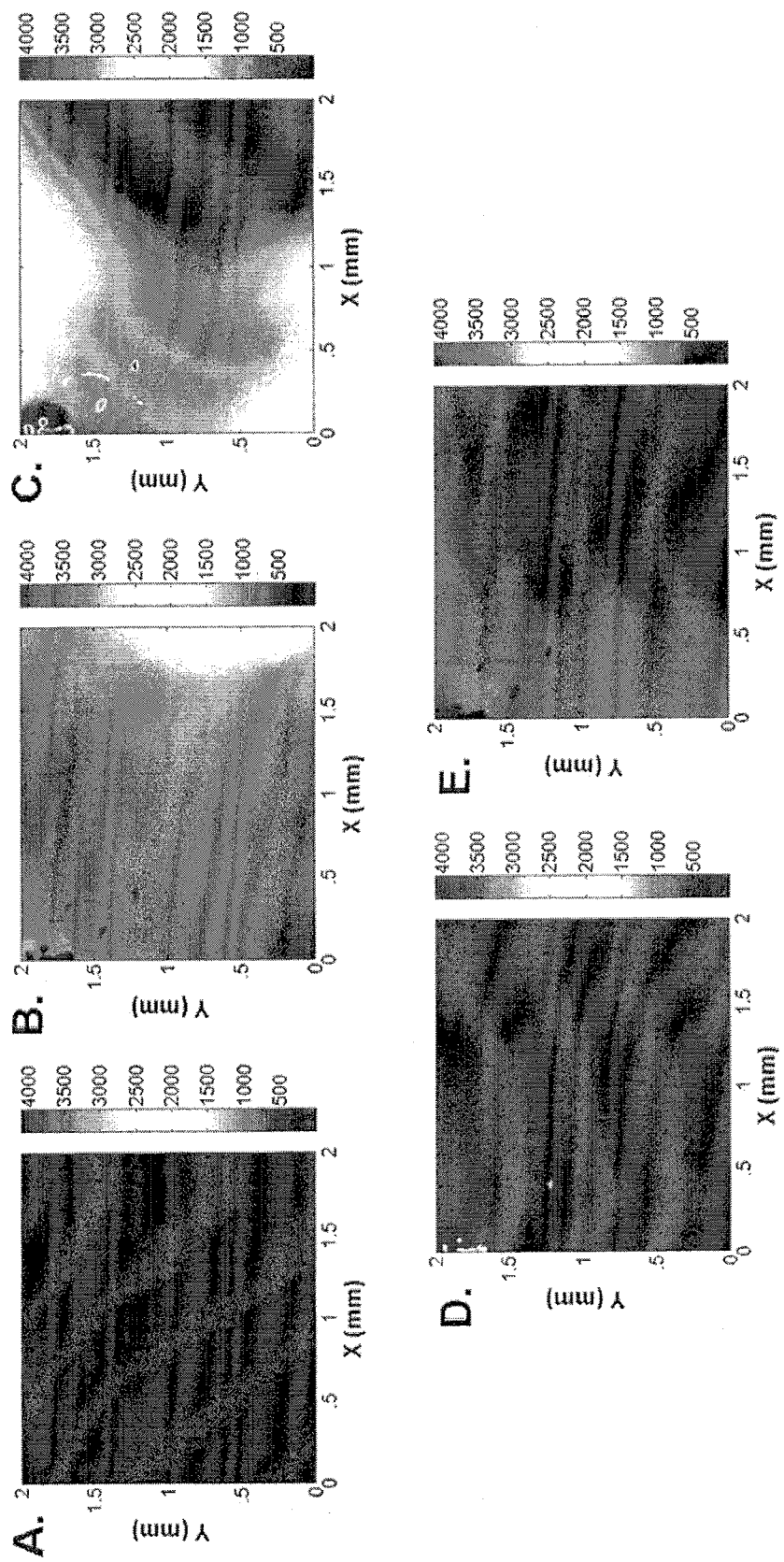
FIG. 9 shows CCD images of chemiluminescent solutions at disjointed on at disjointed 'bow-tie' junction at discrete time intervals. CCD images are collected at a rate of 10 Hz for approximately 10 seconds. Samples are exposed to five second microwave pulse (Mw pulse) that are initiated approximately 2 seconds after data collection. Discrete time intervals are labeled as A) 0 seconds or steady state emission B) emission upon initial exposure to microwave pulse C)

During image collection, samples were exposed to five second microwave pulses. The pre-microwave fluorescence intensity is averaged over a 100 pixel$^2$ region selected from the center of the image (FIG. 5. insets, box outlines). The average intensity vs. time data of the CCD images for the 10 μM Ru(by)$_2$Cl$_2$ solution at disjointed 'bow-tie' junction and on plain glass slides (control) is normalized with respect to the maximum pre-microwave fluorescence intensity (FIG. 5) and scaled to the pre-calibrated room temperature normalized intensity (FIGS. 3 and 9 at RT). During exposure to the microwave pulse, a slight decrease in the fluorescence intensity was observed of the 10 μM Ru(by)$_2$Cl$_2$ solutions on the glass substrates, which corresponds to a temperature increase of about 5-8° C. (FIG. 5—top right, inset). On the other hand, a significant decrease in the fluorescence intensity was observed of the 10 μM Ru(by)$_2$Cl$_2$ solutions in the gap of a 'bow-tie' geometry during exposure to the microwave pulse (FIG. 5—bottom right, inset), recalling that emission is inversely proportional to temperature.

Figure 6:
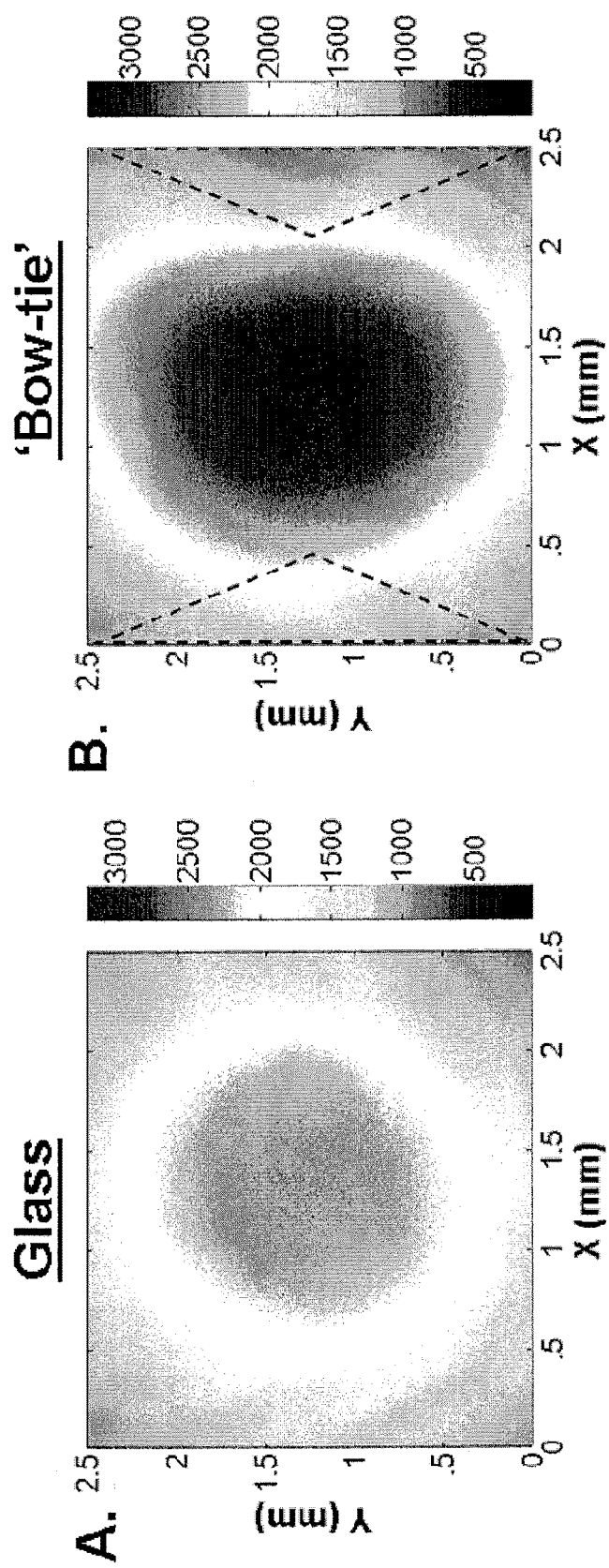
FIG. 6 shows real time movies of the decrease in fluorescence intensity of 10 µM $Ru(by)_2Cl_2$ solutions during exposure to five second microwave pulse on A) plain glass substrates B) glass substrates modified with vapor deposited gold 'bow-tie' structures 75 nm demonstrate the functionality of the fluorescence microscope in a microwave cavity.

With respect to calibration curve of the 10 μM Ru(by)$_2$Cl$_2$ solutions intensity versus temperature, the temperature of the solutions on the glass substrate rose slightly above room temperature (FIG. 3, Glass), while the change in intensity of the 10 μM Ru(by)$_2$Cl$_2$ solutions in the gap of a 'bow-tie' geometry corresponds to a dramatic temperature decrease that is outside the linear range of the temperature versus intensity plot (FIG. 3, dashed line). Real time movies of the decrease in fluorescence intensity of these solutions during exposure to a low power microwave pulse are shown here to demonstrate the functionality of the fluorescence microscope in a microwave cavity, as shown in FIG. 6 A,B.

Figure 7:
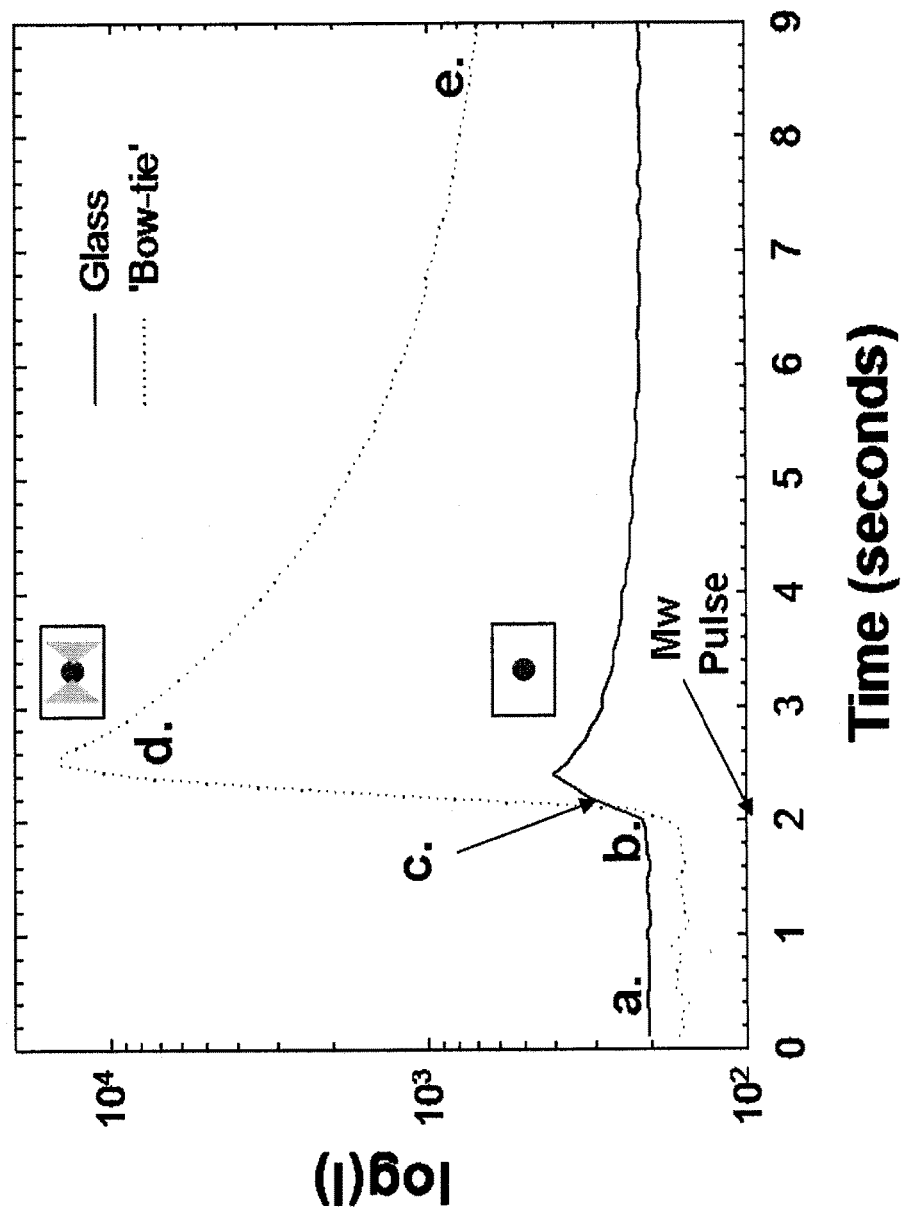
FIG. 7 shows maximum pixel intensity time traces from chemiluminescent solutions on plain glass slides (control) and in the gap of a disjointed 'bow-tie' geometry 75 nm thick. CCD images are collected at a rate of 10 Hz for approximately 10 seconds. Samples are exposed to five second microwave pulse (Mw pulse) that are initiated approximately 2 seconds after data collection. Discrete time intervals are labeled as a) 0 seconds or steady state emission b) emission upon initial exposure to microwave pulse c) during the application of the microwave pulse and d) maximum 'triggered' emission e) final emission.
Figure 8:
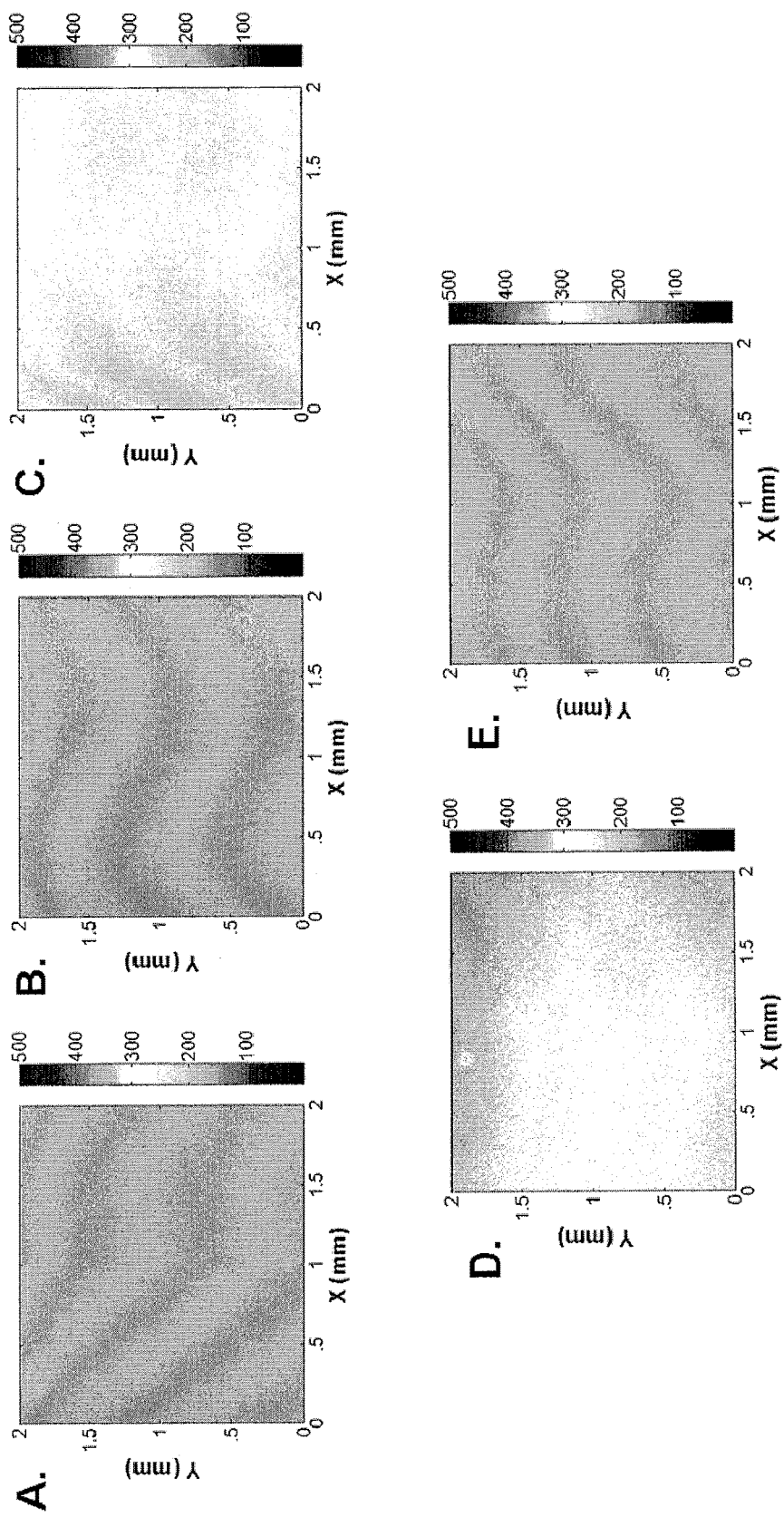
FIG. 8 shows CCD images of chemiluminescent solutions at disjointed on plain glass slides (control) at discrete time intervals. CCD images are collected at a rate of 10 Hz for approximately 10 seconds. Samples are exposed to five second microwave pulse (Mw pulse) that are initiated approximately 2 seconds after data collection. Discrete time intervals are labeled as A) 0 seconds or steady state emission B) emission upon initial exposure to microwave pulse C) during the application of the microwave pulse and D) maximum 'triggered' emission E) final emission.

In addition to real-time imaging of temperature dependent Ru(by)$_2$Cl$_2$ solutions, the local 'triggering' of chemiluminescent solutions was also imaged to further validate the effectiveness of the microscope in a microwave concept. 6 μl of blue chemiluminescence solution was placed in an imaging well affixed to plain glass substrates and in the 2 mm gap of the continuous gold thin film bow-tie' geometry [23, 30]. The chemiluminescence emission was recorded over at a frame rate of 10 Hz for 10 seconds (FIG. 7). During the 10 second time interval, samples were exposed to a five second microwave pulse, which induces the 'triggered' emission or dramatic rise in the maximum photon flux, as shown in FIG. 7.

Discrete time points are labeled in FIG. 7 and correspond to a) steady state emission b) emission upon initial exposure to microwave pulse c) during the onset of microwave pulse d) maximum 'triggered' emission during pulse and e) final microwave emission. During recording of the disjointed 'bow-tie' geometries intensity images, the CCD camera gain was decreased by about a factor of 4.5 to prevent saturation. Subsequently, the resulting CCD pixel intensities for the 'bow-tie' geometry are scaled accordingly to derive an absolute comparison to recorded chemiluminescence intensities from the glass substrates. CCD images of the chemiluminescence emission at these discrete time points are shown for the plain glass substrates (FIG. 8) and at the disjointed 'bow-tie junction (FIG. 9).

Pixel intensity scales for the both glass and 'bow-tie' images are equivalent to accurately reflect the dramatic increase in 'on-demand' photon flux from the chemiluminescent reactions. Again, real time movies of the increase in 'photon flux' form the chemiluminescence solutions during exposure to a low power microwave pulse are shown here to demonstrate the functionality of the fluorescence microscope in a microwave, as shown in FIG. 10 A,B.

The feasibility of constructing a fluorescence microscope in a microwave cavity has been demonstrated herein. Using this optical configuration, microwave induced real-time temperature decreases in 10 μM Ru(by)$_2$Cl$_2$ solutions were observed on plain glass substrates and in proximity to discrete planar structure geometries. The chemiluminescence emission results show approximately 100-fold increases in chemiluminescence emission from the 'bow-tie' geometry. With regards to the 'triggering of the chemiluminescent reactions, the 'triggered' emission commences from the side that is closest to the incident microwave field generated by the magnetron. The CCD images of the chemiluminescent solutions depict the acceleration of the chemiluminescent reactions due to microwave heating or dielectric loss to the chemiluminescence solution. Since the right side of the image (FIG. 9B) is oriented closest to the magnetron, it is seen that the 'triggered' emission commence from the side closest to the microwave source. In a subsequent image (FIG. 9C), it was observed that the triggered emission from the wave reflected from the far wall of the cavity (Note: a standing wave is created in the cavity). It is important to note that the 'bow-tie' tips are slightly offset to facilitate the viewing of 'triggered' emission that results from reflected waves in a microwave cavity.

Using the herein described microwave focused and triggering technologies, the feasibility of capturing real-time images of microwave induced solution heating and accelerated chemiluminescence reactions was demonstrated.

REFERENCES

The contents of the references discussed herein are incorporated by reference herein for all purposes.
1. V. Sridar, "Rate acceleration of Fischer-indole cyclization by microwave irradiation," *Indian Journal of Chemistry Section B-Organic Chemistry Including Medicinal Chemistry* 36, 86-87 (1997).
2. "Technology Vision 2020," (The U.S. Chemical Industry, 1996).
3. V. Sridar, "Microwave radiation as a catalyst for chemical reactions," *Current Science* 74, 446-450 (1998).
4. R. S. Varma, "Advances in Green chemistry: Chemical Synthesis using Microwave Irradiation," (Astrazeneca Research Foundation, India, Bangalore, 2002).
5. C. O. Kappe, "High-speed combinatorial synthesis utilizing microwave irradiation," *Current Opinion in Chemical Biology* 6, 314-320 (2002).
6. D. Adam, "Microwave chemistry: Out of the kitchen," *Nature* 421, 571-572 (2003).
7. K. Aslan, S. N. Malyn, and C. D. Geddes, "Multicolor Microwave-Triggered Metal-Enhanced Chemiluminescence," *J Am. Chem. Soc.* 128, 13372-13373 (2006).
8. R. S. Varma, "Solvent-free organic syntheses—using supported reagents and microwave irradiation," *Green Chemistry* 1, 43-55 (1999).
9. I. Roy, and M. N. Gupta, "Applications of microwaves in biological sciences," *Current Science* 85, 1685-1693 (2003).
10. R. Gedye, F. Smith, K. Westaway, H. Ali, L. Baldisera, L. Laberge, and J. Rousell, "The Use of Microwave-Ovens for Rapid Organic-Synthesis," *Tetrahedron Letters* 27, 279-282 (1986).
11. S. Jain, S. Sharma, and M. N. Gupta, "A microassay for protein determination using microwaves," *Analytical Biochemistry* 311, 84-86 (2002).
12. A. G. Whittaker, and D. M. P. Mingos, "Microwave-assisted solid-state reactions involving metal powders," *J Chem. Soc. Dalton Trans.* 12, 2073-2079 (1995).
13. S. Caddick, "Microwave assisted organic reactions," *Tetrahedron* 51, 10403-10432 (1995).

14. M. Pagnotta, C. L. F. Pooley, B. Gurland, and M. Choi, "Microwave Activation of the Mutarotation of alpha-D-glucose—An Example of an Intrinsic Microwave Effect," *Journal of Physical Organic Chemistry* 6, 407-411 (1993).
15. A. B. Copty, Y. Neve-Oz, I. Barak, M. Golosovsky, and D. Davidov, "Evidence for a specific microwave radiation effect on the green fluorescent protein," *Biophysical Journal* 91, 1413-1423 (2006).
16. A. Shaman, S. Mizrahi, U. Cogan, and E. Shimoni, "Examining for possible non-thermal effects during heating in a microwave oven," *Food Chemistry* 103, 444-453 (2007).
17. R. K. Adair, "Biophysical limits on athermal effects of RF and microwave radiation," *Bioelectromagnetics* 24, 39-48 (2003).
18. K. R. Foster, "Thermal and nonthermal mechanisms of interaction of radiofrequency energy with biological systems," *Ieee Transactions on Plasma Science* 28, 15-23 (2000).
19. R. Weissenborn, K. Diederichs, W. Welte, G. Maret, and T. Gisler, "Non-thermal microwave effects on protein dynamics? An X-ray diffraction study on tetragonal lysozyme crystals," *Acta Crystallographica Section D-Biological Crystallography* 61, 163-172 (2005).
20. H. Bohr, and J. Bohr, "Microwave-enhanced folding and denaturation of globular proteins," *Physical Review E* 61, 4310-4314 (2000).
21. J. Gellermann, W. Wlodarczyk, B. Hildebrandt, H. Ganter, A. Nicolau, B. Rau, W. Tilly, H. Fahling, J. Nadobny, R. Felix, and P. Wust, "Noninvasive magnetic resonance thermography of recurrent rectal carcinoma in a 1.5 Tesla hybrid system," *Cancer Research* 65, 5872-5880 (2005).
22. K. Hamad-Schifferli, J. J. Schwartz, A. T. Santos, S. G. Zhang, and J. M. Jacobson, "Remote electronic control of DNA hybridization through inductive coupling to an attached metal nanocrystal antenna," Nature 415, 152-155 (2002).
23. M. J. R. Previte, and C. D. Geddes, "Spatial and Temporal Control of Microwave Triggered Chemiluminescence: A Rapid and Sensitive Small Molecule Detection Platform," *Analytical Chemistry in preparation* (2007).
24. C. L. R. Catherall, T. F. Palmer, and R. B. Cundall, "CHEMI-LUMINESCENCE FROM REACTIONS OF BIS(PENTACHLOROPHENYL)OXALATE, HYDROGEN-PEROXIDE AND FLUORESCENT COMPOUNDS—KINETICS AND MECHANISM," *Journal of the Chemical Society—Faraday Transactions Ii* 80, 823-836 (1984).
25. O. Filevich, and R. Etchenique, "1D and 2D temperature imaging with a fluorescent ruthenium complex," *Analytical Chemistry* 78, 7499-7503 (2006).
26. B. Durham, J. V. Caspar, J. K. Nagle, and T. J. Meyer, "Photochemistry of Ru(bpy)$_3^{2+}$," *Journal of the American Chemical Society* 104, 4803-4810 (1982).
27. J. Vanhouten, and R. J. Watts, "Temperature-dependence of Photophysical and Photochemical Properties of Tris(2, 2'-bypridyl)Ruthenium(II) Ion in Aqueous Solution," *Journal of the American Chemical Society* 98, 4853-4858 (1976).
28. O. Filevich, and R. Etchenique, "1D and 2D temperature imaging with a fluorescent ruthenium complex," *Analytical chemistry* 78, 7499-7503 (2006).
29. N. A. Nemkovich, A. N. Rubinov, and A. T. Tomin, "Inhomogeneous Broadening of Electronic Spectra of Dye Molecules in Solutions," in *Topics in Fluorescence Spectroscopy, Vol. 2, Principles*, J. R. Lakowicz, ed. (Plenum Press, New York, 1991), pp. 367-428.
30. M. J. R. Previte, and C. D. Geddes, "Microwave-triggered chemiluminescence with planar geometrical aluminum substrates: Theory, simulation and experiment," *Journal of Fluorescence* 17, 279-287 (2007).

That which is claimed is:

1. A microwave/optical imaging system for detecting microwave induced reactions or interactions of biomolecules in a sample, the system comprising:
 a) an enclosed container comprising a microwave cavity having at least one opening therein;
 b) a sample plate positioned within the microwave cavity, wherein the sample plate comprises metallic surfaces adhered on the sample plate surface, wherein the metallic surfaces have a triangular geometric shape wherein a first pointed region of a first triangular shaped metallic surface is adjacent and opposite to a second pointed region of a second triangular shaped metallic surface and having a distance from about 0.01 mm to 5 mm between the first and second point regions, thereby creating a reactive zone therebetween for positioning of the sample therein, wherein the sample further comprises a detector molecule or components of a detectable reaction;
 c) a microwave energy producing source communicatively connected to the microwave cavity for delivering microwave energy into the cavity and directed towards the sample; and
 d) an optical imaging device communicatively connected to the microwave cavity and positioned for directing excitation light from an electromagnetic energy producing source to the sample to excite the sample, and capturing luminescent emissions emitted from an excited sample thereby detecting a microwave induced reaction or interactions of a biomolecule in the sample, wherein the optical imaging device comprises:
 an electromagnetic energy producing source to produce energy at a frequency to excite the sample;
 an objective positioned for focusing electromagnetic energy on the sample;
 a dichroic mirror positioned between the laser and objective for reflecting electromagnetic energy from the energy source to the objective and for directing emitted signals from the excited sample; and
 a tube lens positioned after the dichroic mirror for collecting emissions from the excited sample and directing same to a detector device.

2. The system of claim 1, wherein the microwave cavity includes a stage for holding the sample plate.

3. The system of claim 1, wherein the detector molecule is a fluorophore.

4. The system of claim 1, wherein the delivered microwave energy has a frequency of from 2 GHz to 3 GHz, and a power level in a range between about 10 mwatts and 700 watts.

5. The system of claim 1, wherein the biomolecule is selected from the group consisting of nucleic acids, aromatic carbon ring structures, NADH, FAD, amino acids, proteins, peptides, carbohydrates, steroids, flavins, DNA, RNA, oligonucleotides, nucleic acids, fatty acids, myoglobin, sugar groups such as glucose etc., vitamins, cofactors, purines, pyrimidines, formycin, lipids, phytochrome, phytofluor, peptides, lipids, antibodies and phycobiliproptein.

6. The system of claim 1, wherein the objective captures emitted signal from the excited sample.

7. The system of claim 1, wherein the metallic surfaces comprise silver, gold, copper, zinc, aluminum, or platinum.

8. The system of claim 1, wherein the sample is placed in the reactive zone and contacted by the microwave energy and irradiated by excitation energy.

9. The system of claim 8, wherein the sample plate comprises multiple wells wherein the reactive zone is within the wells and exposure to microwave energy enhances the reactions therein.

10. The system of claim 8, wherein the reactive zone has a distance between the first and second pointed regions ranging from about 2 mm to about 3 mm.

11. The system of claim 1, wherein the sample plate is fabricated of glass or a polymeric material.

\* \* \* \* \*